United States Patent [19]

Ito et al.

[11] Plant 4,518

[45] Apr. 8, 1980

[54] NECTARINE TREE

[76] Inventors: James K. Ito, 369 S. Kings Dr.; James C. Sorensen, 20874 E. Manning Ave., both of Reedley, Calif. 93654

[21] Appl. No.: 943,101

[22] Filed: Sep. 18, 1978

[51] Int. Cl.[2] ..... A01H 5/03

[52] U.S. Cl. ..... Plt./41

[58] Field of Search ..... Plt./41

*Primary Examiner*—Robert E. Bagwill

*Attorney, Agent, or Firm*—Huebner & Worrel

[57] ABSTRACT

A new variety of nectarine discovered as a sport of a Regal Grand growing in Fresno County, located in the San Joaquin Valley of California. The new variety is characterized by fruit which, when mature, is highly colored, keeps well and is particularly suited for shipping.

1 Drawing Figure

BACKGROUND OF THE VARIETY

The present invention relates to a new and distinct variety of nectarine tree of a yellow-fleshed, clingstone fruit type which was discovered by us as a bud sport on a "Regal Grand" nectarine tree, U.S. Plant Pat. No. 1,751.

ORIGIN AND ASEXUAL REPRODUCTION OF THE NEW VARIETY

At the time of our discovery of the sport, above referred to, two limbs bearing the fruit of the new variety were observed growing on a Regal Grand nectarine tree in a ten acre orchard of about 1,000 trees, located on the south side of Manning Avenue, between Alta and Crawford streets, near Reedley, County of Fresno, State of California. The fruit was picked and stored by us in order to determine its keeping characteristics, and steps were taken to protect the sport limbs.

In early 1975 we asexually reproduced one tree from bud wood taken from the sport limbs by grafting over root stock of a Late LeGrand nectarine tree, located in a test plot near Reedley. In 1976 additional trees were made from bud wood taken from the asexually reproduced tree. The sport limbs, the grafted-over Late LeGrand nectarine tree and the additional trees have been continuously observed.

Contined observations of the sport, as well as the asexual reproductions thereof, confirmed to us that the new variety is different from the Regal Grand, by virtue of size, and coloring and the consistent earlier coloring of the fruit produced thereby.

SUMMARY OF THE NEW VARIETY

In particular, the fruit of the new variety is large, generally uniform, colors early and fully ripens about three weeks later. When the fruit is mature, the skin thereof is predominantly bright red over yellow and displays a prominent yellow suture stripe. The fruit begins to color earlier than the Regal Grand and continues to darken until fully ripe. The suture stripe tends to fade as the fruit reaches full maturity. The fruit keeps well on the tree, thus providing for a long harvest period. The high red coloring and the good keeping qualities make our new variety especially desirable for commercial fruit productions.

BRIEF DESCRIPTION OF THE DRAWING

The accompanying drawing illustrates typical specimens of the fruit and foliage of our new variety, as grown in the San Joaquin Valley of California. One specimen is shown in cross-section for purposes of illustrating the stone and flesh thereof; two other specimens are shown in mutually inverted relation for illustrating size, form and skin coloring; and the foliage is shown to illustrate typical leaf size, form and glandular characteristics of our new variety.

DETAILED DESCRIPTION

The following is a detailed description of our new variety with color terminology being in accordance with the Nickerson Color Fan, obtainable from Munsell Color Company, Baltimore 2, Md., except in instances where terminology having generally accepted meaning is employed.

Parentage: Bud sport of "Regal Grand", patented variety.

Propagation: Maintains its distinguishing characteristics through succeeding asexual propagations.

Locality where grown and observed: Near Reedley, County of Fresno, Calif.

TREE

Size: Large.

Vigor: Vigorous; very productive.

Regularity of bearing: A regular bearer.

Trunk: Medium to large size, similar to the Regal Grand.

Branches: Color of old wood, 5 YR 3/3, moderate brown over 10 YR 5/6, strong yellowish brown; new wood tends toward a slight reddish green.

Leaves:

*Color.*—Moderate olive green 2.5 GY 4/3.

*Size.*—Medium, average length 5 inches and average width 1.1 inches.

*Shape.*—Lanceolate, with acuminate tip and base.

*Marginal form.*—Crenate.

*Glandular characteristics.*—One to four, small to medium, reniform glands, found mostly on base of leaf.

*Petiole.*—Medium, approximately 0.5 inches in length and 0.1 inches in thickness.

*Stipules.*—None.

Flower bud: Similar in size, shape and color to those of the Regal Grand variety.

Flower: Similar in size, shape, color and blossom dates to those of the Regal Grand variety.

FRUIT

Maturity: Colors during the first week of August, about the fourth, but does not fully ripen until about three weeks later, about the 25th of August, and is considered to be ready for shipping about one week later than the fruit of the Regal Grand variety.

Size:

*Uniformity.*—Generally large and uniform, considered to be larger than the fruit of the Regal Grand variety. While the description of the fruit size of Regal Grand in U.S. Plant Pat. No. 1,751 would lead one to believe that the fruit size of the sport is smaller than the former, just the opposite was observed when the parent and sport were compared under the same growing conditions.

*Axial diameter.*—Three inches in the plane of the suture.

*Transverse diameter.*—Two and one-half inches in plane of suture.

*Transverse diameter at right angles to suture plane*.—Two and one-half inches.

Form: Mostly uniform in shape, slightly elongated ovate and characterized by slight protrusion of lips.

*Tendency to split.*—Slight to none.

*Tendency to crack.*—None.

*Base.*—Oblate.

*Apex.*—Rounded with point at apex, located in suture.

*Suture.*—Prominent, extends from stem cup beyond pistil point and is characterized by a distinctive yellow suture stripe throughout its length during early maturity; and suture lips tend to be unequally protruded.

Stem: About 0.25 inches in length and about 0.2 inches in diameter.

Skin:

*Thickness.*—Thick and smooth.

*Color.*—Predominantly 5 R 4/12 strong red to 5 R 3/7 dark red over 10 YR 8/10 moderate orange yellow, during earlier stages of ripening, the orange yellow coloring being well overspread by the strong red, particularly near the apex end which tends to darken to 2.5 R 3/7 dark red, as the fruit fully matures.

*Suture stripe.*—10 YR 8/10 moderate orange yellow which tends to fade as the fruit approaches full maturity.

*Pubescence.*—None.

Flesh:

*Texture.*—Firm and crisp.

*Color.*—2.5 Y 9/9 brilliant yellow color changing to 2.5 R 3/7 dark red near the stone.

*Juice.*—Moderate to abundant.

*Flavor.*—Generally sweet; but slightly tart.

*Aroma.*—Mild.

*Fibers.*—Few.

*Ripening.*—Tends to ripen evenly.

*Eating quality.*—Excellent.

Stone:

*Adherence to flesh.*—Tenacious, adheres to flesh.

*Size.*—Large, average size 1.05 inches in length, 1.25 inches in width, and 0.9 inches in thickness.

*Form.*—Mostly ovate and generally symmetrical with respect to longitudinal planes, further characterized by an acuminate tip, straight base and rounded sides of substantially equal lengths.

*Hilum.*—Oval to oblong.

*Dorsal edge.*—Thin, having a groove extending from the hilum to the apex.

*Ventral edge.*—Slightly thicker than the dorsal edge with deep grooves toward the base end.

*Surface.*—Furrowed toward the apex end and pitted toward the base end.

*Color.*—2.5 YR 5/9 brownish orange, when dry.

Use: Shipping.

Keeping quality: Very good.

Shipping quality: Very good.

Resistance to disease: About the same as that of the Regal Grand variety.

Although the new variety of nectarine tree possesses the described characteristics as a result of the growing conditions in Fresno County, Calif., in the central portion of the San Joaquin Valley, it is to be understood that variations of the usual magnitude in characteristics incident to growing conditions, fertilization, pruning and pest control are to be expected.

Having thus described and illustrated our new variety of nectarine tree, what is new and desired to be secured by Letters Patent is:

1. A new and distinct variety of nectarine tree, substantially as illustrated and described, which generally is of a larger size and more vigorous than the Regal Grand variety, of which it is a sport, and which is a heavy and regular bearer of large, uniform, clingstone, globose to slightly oblong fruit having firm yellow flesh and yellow skin substantially overspread with bright red at maturity, reached approximately seven to ten days later than the fruit of the Regal Grand nectarine variety, the fruit of the new variety being particularly characterized by a prominent suture extended from the stem cup of the fruit to beyond the pistil point and displaying a yellow suture stripe until final stages of ripening.

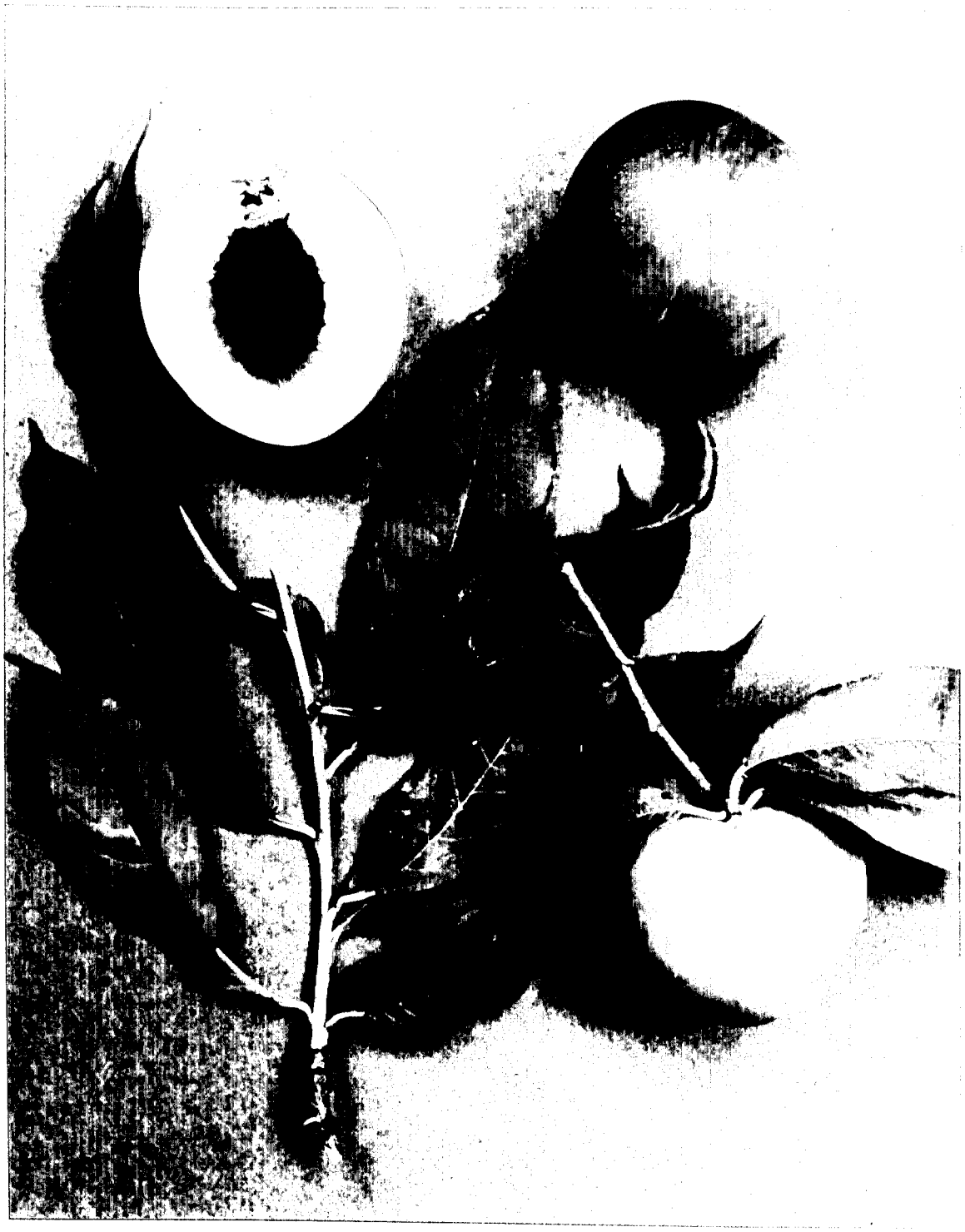

* * * * *